(12) United States Patent
Song et al.

(10) Patent No.: US 10,603,517 B2
(45) Date of Patent: Mar. 31, 2020

(54) ION BEAM TREATMENT APPARATUS

(71) Applicant: ELECTRONICS AND TELECOMMUNICATIONS RESEARCH INSTITUTE, Daejeon (KR)

(72) Inventors: Dong Hoon Song, Daejeon (KR); Moon Youn Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 16/007,923

(22) Filed: Jun. 13, 2018

(65) Prior Publication Data
US 2018/0361173 A1 Dec. 20, 2018

(30) Foreign Application Priority Data

Jun. 15, 2017 (KR) .......................... 10-2017-0076053
May 24, 2018 (KR) .......................... 10-2018-0058985

(51) Int. Cl.
*A61N 5/10* (2006.01)
*H01J 37/075* (2006.01)
*G21K 1/08* (2006.01)
*G21K 5/04* (2006.01)

(52) U.S. Cl.
CPC .............. *A61N 5/1077* (2013.01); *G21K 1/08* (2013.01); *G21K 5/04* (2013.01); *H01J 37/075* (2013.01); *A61N 2005/1088* (2013.01); *A61N 2005/1095* (2013.01); *H01J 2237/0825* (2013.01)

(58) Field of Classification Search
CPC ... H01J 37/085; A61N 5/1077; A61N 5/1081; A61N 5/1082; A61N 5/1085; A61N 5/1087
USPC ............................................ 250/492.1, 492.3
See application file for complete search history.

(56) References Cited

U.S. PATENT DOCUMENTS

| | | | |
|---|---|---|---|
| 8,878,464 B2 | 11/2014 | Clayton et al. | |
| 2009/0050819 A1* | 2/2009 | Ma | A61N 5/10 250/396 ML |
| 2013/0033695 A1* | 2/2013 | Kong | F41H 13/0062 356/28 |
| 2013/0261369 A1 | 10/2013 | Jung et al. | |
| 2013/0289331 A1 | 10/2013 | Jung et al. | |
| 2017/0157428 A1* | 6/2017 | Lee | A61N 5/1049 |

FOREIGN PATENT DOCUMENTS

| | | |
|---|---|---|
| EP | 2363170 B1 | 1/2014 |
| KR | 10-2014-0063192 A | 5/2014 |
| KR | 10-2015-0108025 A | 9/2015 |

* cited by examiner

*Primary Examiner* — Jason L McCormack (57) ABSTRACT

Provided is an ion beam treatment apparatus. The ion beam treatment apparatus includes a laser generation unit, a dividing part dividing a pulse laser beam generated in the laser generation unit into a first laser beam and a second laser beam, a first target part receiving the first laser beam from the dividing part to generate a first ion beam, a second target part receiving the second laser beam from the dividing part to generate a second ion beam, a first path adjusting part adjusting a path of the first ion beam to irradiate the first ion beam to a treated patient, and a second path adjusting part adjusting a path of the second ion beam to irradiate the second ion beam to the treated patient.

18 Claims, 5 Drawing Sheets

ION BEAM TREATMENT APPARATUS

CROSS-REFERENCE TO RELATED APPLICATIONS

This U.S. non-provisional patent application claims priority under 35 U.S.C. § 119 of Korean Patent Application No. 10-2017-0076053, filed on Jun. 15, 2017, and Korean Patent Application No. 10-2018-0058985, filed on May 24, 2018, in the Korean Intellectual Property Office, the entire contents of which are hereby incorporated by reference.

BACKGROUND

The present disclosure herein relates to an ion beam treatment apparatus, and more particularly, to an ion beam treatment apparatus using a laser-based proton beam.

X-ray treatment and gamma-ray treatment, which account for the majority of radiation treatment currently used for cancer treatment, often leave aftereffects such as subsequent cancer development because they leave radiation exposure to normal tissues, which occurs during the treatment process. Since the essence of X-rays or gamma rays is light rays, when absorbed into the human body, much amount is absorbed in the epidermis, and the amount of absorption decreases as it penetrates deep into the human body. In contrast, when particles are accelerated to be injected into the human body, the particles coming into contact with the inside of the human body while progressing to the inside of the human body may be ionized to lose energy. However, when the particles continuously progresses into the human body, a cross-section indicating probability of absorbing the injected particles is stepped while increasing, and a degree of integration of the injected particles immediately before being stopped exhibits a maximum value (Bragg peak).

Recently, a treatment method using proton beams is being studied as a method for application to cancer treatment in internal organs of the human body. For example, studies on a treatment method for treating the periphery of the cancerous sits by using proton beams to prevent cancer cells from being metastasized. The proton beams may be acquired through a particle accelerator in the beginning of the study. In hospitals, protons generated through a large accelerator may be controlled through a gantry so as to be used for the treatment.

SUMMARY

The present disclosure provides an ion beam treatment apparatus that is capable of irradiating a plurality of ion beams.

The present disclosure provides an ion beam treatment apparatus that is capable of improving treatment efficiency.

An object of the present disclosure is not limited to the aforesaid, but other objects not described herein will be clearly understood by those skilled in the art from descriptions below.

An embodiment of the inventive concept provides an ion beam treatment apparatus including: a laser generation unit; a dividing part dividing a pulse laser beam generated in the laser generation unit into a first laser beam and a second laser beam; a first target part receiving the first laser beam from the dividing part to generate a first ion beam; a second target part receiving the second laser beam from the dividing part to generate a second ion beam; a first path adjusting part adjusting a path of the first ion beam to irradiate the first ion beam to a treated patient; and a second path adjusting part adjusting a path of the second ion beam to irradiate the second ion beam to the treated patient.

In an embodiment, the ion beam treatment apparatus may further include: a first amplifying part amplifying the first laser beam between the dividing part and the first target part, and a second amplifying part amplifying the second laser beam between the dividing part and the first target part.

In an embodiment, a pulse of the first laser beam amplified by the first amplifying part and a pulse of the second laser beam amplified by the second amplifying part may be shifted within one period of a pulse of the pulse laser beam.

In an embodiment, the pulse of the first laser beam amplified by the first amplifying part and the pulse of the second laser beam amplified by the second amplifying part may be shifted by about ½ period of the pulse of the pulse laser beam.

In an embodiment, the first laser beam and the second laser beam may travel in directions opposite to each other with respect to the dividing part.

In an embodiment, the first path adjusting part and the second path adjusting part may rotate with the same rotation axis. In an embodiment, each of the first path adjusting part and the second path adjusting part may rotate around the treated patient.

In an embodiment, the rotation path of the first path adjusting part and the rotation path of the second path adjusting part may do not overlap each other.

In an embodiment, the ion beam treatment apparatus may further include a light focusing part disposed between the first target part and the first path adjusting part or between the second target part and the second path adjusting part.

In an embodiment, the dividing part may include a switching mirror.

In an embodiment, the ion beam treatment apparatus may further include a light collecting part disposed between the first amplifying part and the first target part or between the second amplifying part and the second target part.

In an embodiment of the inventive concept, an ion beam treatment apparatus includes: a switching mirror receiving a pulse laser from a laser generation unit; a target part receiving a first laser beam and a second laser beam from the switching mirror, wherein the target part receives the first laser beam and the second laser beam to generate a first ion beam and a second ion beam; a path adjusting part controlling paths of the first ion beam and the second ion beam to irradiate the first and second ion beams to a treated patient; and a patient support unit on which the treated patient is located.

In an embodiment, the path adjusting part may include: a first path adjusting part providing a path along which the first ion beam travels, and a second path adjusting part providing a path along which the second ion beam travels.

In an embodiment, the traveling path of the first ion beam may do not overlap the traveling path of the second ion beam.

In an embodiment, the first path adjusting part and the second path adjusting part may be opposite to each other with respect to the treated patient.

In an embodiment, the first path adjusting part and the second path adjusting part may rotate around the treated patient.

In an embodiment, the laser generating part, the switching mirror, and the target part may be provided in a beam generation unit below the patient support unit.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Exemplary embodiments of the inventive concept will be described with reference to the accompanying drawings so as to sufficiently understand constitutions and effects of the inventive concept. The present disclosure may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. A person with ordinary skill in the technical field of the present invention pertains will be understood that the present invention can be carried out under any appropriate environments.

In the following description, the technical terms are used only for explaining a specific exemplary embodiment while not limiting the inventive concept. In this specification, the terms of a singular form may include plural forms unless specifically mentioned. The meaning of 'comprises' and/or 'comprising' specifies a component, a step, an operation and/or an element does not exclude other components, steps, operations and/or elements.

In the specification, it will be understood that when a layer (or film) is referred to as being 'on' another layer or substrate, it can be directly on the other layer or substrate, or intervening layers may also be present.

Also, though terms like a first, a second, and a third are used to describe various regions and layers (or films) in various embodiments of the inventive concept, the regions and the layers are not limited to these terms. These terms are used only to discriminate one region or layer (or film) from another region or layer (or film). Therefore, a layer referred to as a first layer in one embodiment can be referred to as a second layer in another embodiment. An embodiment described and exemplified herein includes a complementary embodiment thereof. Like reference numerals refer to like elements throughout.

Unless terms used in embodiments of the present invention are differently defined, the terms may be construed as meanings that are commonly known to a person skilled in the art.

Figure 1:
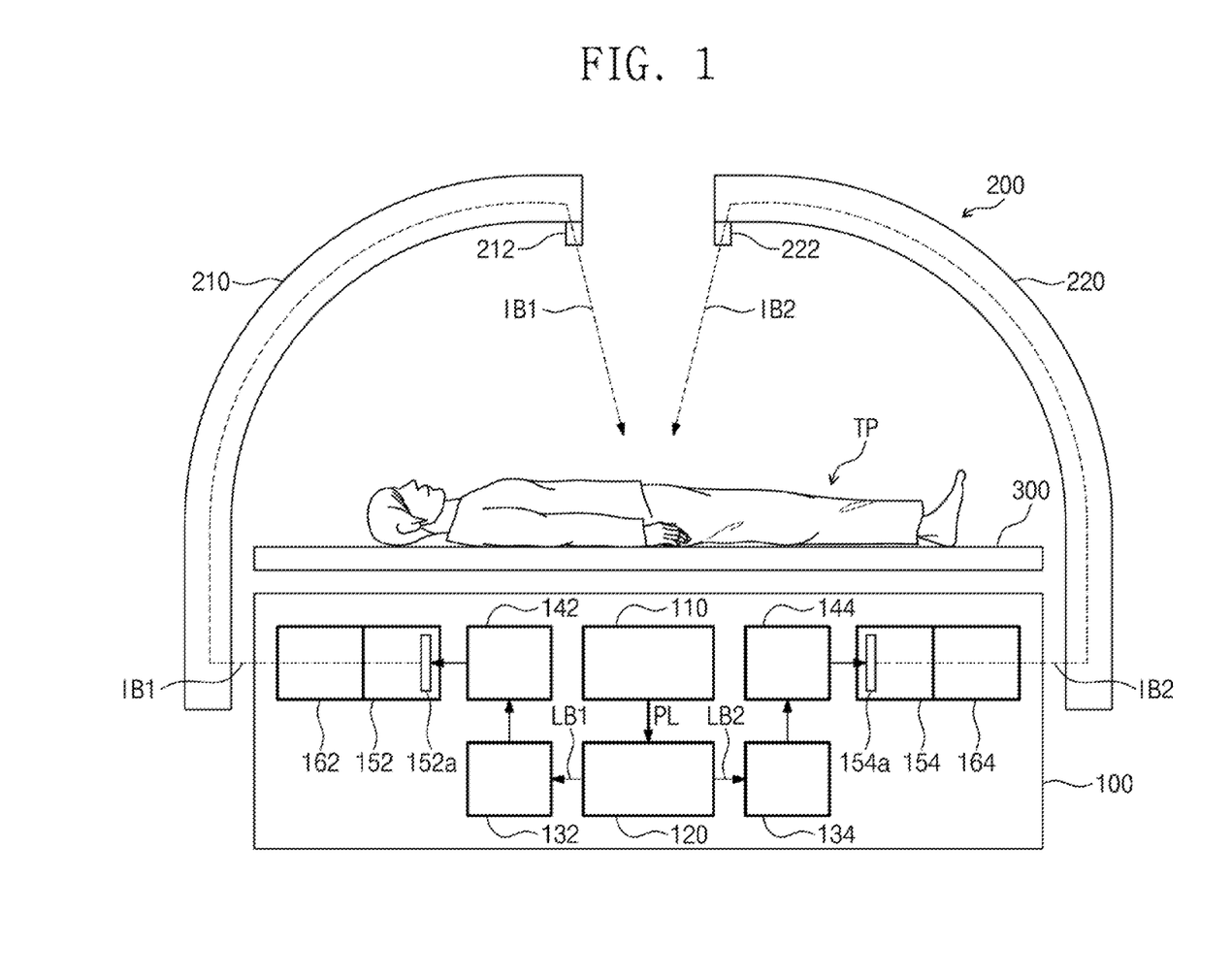
FIG. 1 illustrates a conceptual view for explaining an ion beam treatment apparatus according to embodiments of the inventive concept.
Figure 2:
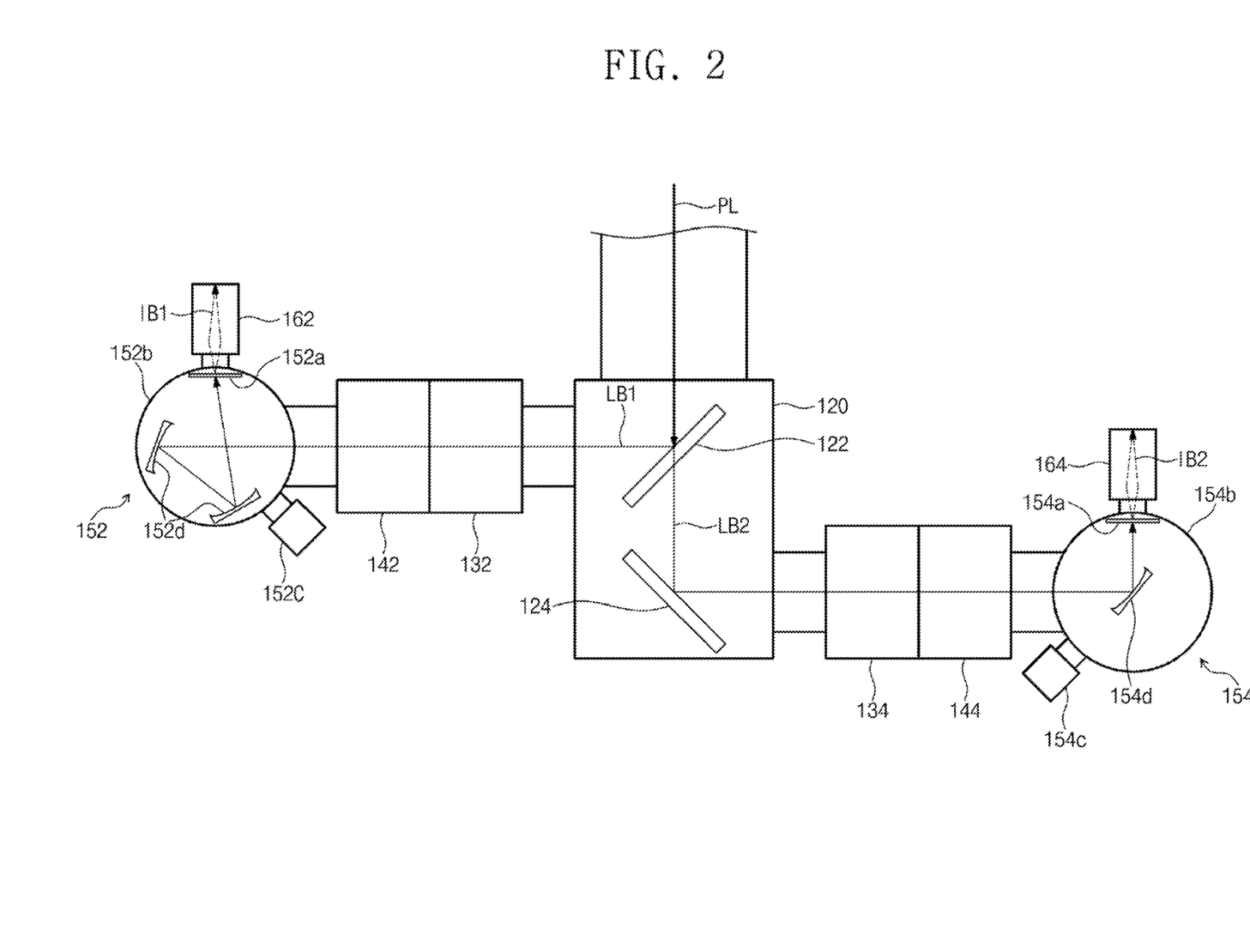
FIG. 2 illustrates a schematic view for explaining a beam generation unit.

Hereinafter, an ion beam treatment apparatus according to the concept of the inventive concept will be described with reference to the accompanying drawings. FIG. 1 is a conceptual view for explaining an ion beam treatment apparatus according to embodiments of the inventive concept. FIG. 2 is a schematic view for explaining a beam generation part.

Referring to FIGS. 1 and 2, an ion beam treatment apparatus may include a beam generation unit 100, a beam transmission unit 200, and a patient support unit 300. The beam generation unit 100 may generate a plurality of ion beams IB1 and IB2 from a pulse laser PL, and the beam transmission unit 200 may receive the ion beams IB1 and IB2 to irradiate each of the ion beams IB1 and IB2 to a target point on the patient support unit 300.

The beam generation unit 100 may include a laser generating part 110, a dividing part 120, amplifying parts 132 and 134, light collecting parts 142 and 144, target parts 152 and 154, and light focusing parts 162 and 164.

The laser generating part 110 may generate a pulse laser beam PL. The laser beam PL generated from the laser generating part 110 may have a period of about 0.1 Hz to about 1,000 Hz. That is, the pulse laser beam PL may have a pulse interval of about 0.001 seconds to about 10 seconds.

The dividing part 120 may divide the pulse laser beam PL generated in the laser generating part 110 into a first laser beam LB1 and a second laser beam LB2. The first laser beam LB1 and the second laser beam LB2 divided in the dividing part 120 may travel in different directions. For example, the first laser beam LB1 and the second laser beam LB2 may travel in directions opposite to each other. As illustrated in FIG. 2, the dividing part 120 may include a first mirror 122 and a second mirror 124. The first mirror 122 may be a switching mirror. A portion of the pulse laser beam PL reflected by the first mirror 122 may be the first laser beam LB1. The other portion of the pulse laser beam PL transmitted through the first mirror 122 may be the second laser beam LB2. The traveling direction of the first laser beam LB1 may be adjusted through the first mirror 122. The traveling direction of the second laser beam LB2 may be adjusted through the second mirror 124. Although the dividing part 120 divides the pulse laser beam PL by using the switching mirror in FIG. 2, the embodiment of the inventive concept is not limited thereto. For example, the dividing part 120 may include various units for dividing the pulse laser beam PL.

The amplifying parts 132 and 134 may amplify the laser beams LB1 and LB2 transmitted from the dividing part 120. In detail, the amplifying parts 132 and 134 may include a first amplifying part 132 provided in a path of the first laser beam LB1 and a second amplifying part 134 provided in a path of the second laser beam LB2. The first and second amplifying parts 132 and 134 may amplify the first laser beam LB1 and the second laser beam LB2, respectively. For example, the first and second amplifying parts 132 and 134 may be chirped pulse amplification (CPA) type of amplifying parts. The transmission of the second laser beam LB2 of the second amplifying part 134 may a time delay with respect to that of the first laser beam LB1 of the first amplifying part 132. Here, the time delay may be less than the pulse interval of the pulse laser beam PL. For example, the first laser beam LB1 and the second laser beam LB2 may be oscillated with a predetermined time delay with respect to each other from the first amplifying part 132 and the second amplifying part 134. That is, a pulse of the first laser beam LB1 amplified by the first amplifying part 132 and a pulse of the second laser beam LB2 amplified by the second amplifying part 134 may be shifted with one period with respect to each other. For example, the time delay may be about ½ of the pulse interval of the pulse laser beam PL. That is, the pulse of the first laser beam LB1 amplified by the first amplifying part 132 and the pulse of the second laser beam LB2 amplified by the second amplifying part 134 may be shifted at about ½ period with respect to each other.

The light collecting parts 142 and 144 may focus the laser beams LB1 and LB2 transmitted from the amplifying parts 132 and 134. In detail, the light collecting parts 142 and 144 may include a first light collecting part 142 provided in the path of the first laser beam LB1 and a second light collecting part 144 provided in the path of the second laser beam LB2. The first and second light collecting parts 142 and 144 may compress the first laser beam LB1 and the second laser beam LB2, respectively. For example, each of the first and second light collecting parts 142 and 144 may include a diffraction grating, a prism, or an aspherical mirror. The first and second light collecting parts 142 and 144 may change the path of the first laser beam LB1 and the path of the second laser beam LB2 as necessary, respectively. Although the laser beams LB1 and LB2 travel to the light collecting parts 142 and 144 via the amplifying parts 132 and 134 in the above description, the embodiment of the inventive concept is not limited thereto.

The target parts 152 and 154 may receive the laser beams LB1 and LB2 to generate the ion beams IB1 and IB2. In detail, the target parts 152 and 154 may include a first target part 152 receiving the first laser beam LB1 to generate the first ion beam IB1 and a second target part 154 receiving the second laser beam LB2 to generate the second ion beam IB2. The first target part 152 may include a first chamber 152b and a first target material 152a within the first chamber 152b. The inside of the first chamber 152b may be maintained in a vacuum state by a first vacuum chamber 152c. The first laser beam LB1 incident into the first chamber 152b may be induced to the first target material 152a. For example, a separate reflection mirror 152d may be provided in the first chamber 152b. Alternatively, unlike FIG. 2, the first light collecting part 142 may be provided together within the first chamber 152b. The first ion beam IB1 may be generated from the first target material 152a by the first laser beam LB1 that is focused onto one surface of the first target material 152a. The first ion beam IB1 may be a proton ion beam. The second target part 154 may include a second chamber 154b and a second target material 154a within the second chamber 154b. The inside of the second chamber 154b may be maintained in a vacuum state by a second vacuum chamber 154c. The second laser beam LB2 incident into the second chamber 154b may be induced to the second target material 154a. For example, a separate reflection mirror 154d may be provided in the second chamber 154b. Alternatively, unlike FIG. 2, the second light collecting part 144 may be provided together within the second chamber 154b. The second ion beam IB2 may be generated from the second target material 154a by the second laser beam LB2 that is focused onto one surface of the second target material 154a. The second ion beam IB2 may be a proton ion beam. The first target material 152a and the second target material 154a may include photoconductive materials in which electron transitions occur by the laser beams LB1 and LB2, respectively. According to an embodiment, each of the photoconductive materials may be a semiconductive material. For example, the semiconductor material includes silicon or germanium. According to another embodiment, each of the photoconductive materials may be hydrocarbon. For example, the hydrocarbon may include graphene or carbon nanotube (CNT). According to further another embodiment, each of the photoconductive materials may be a polymer material. For example, the polymer material may include polyvinyl carbazole.

The light focusing parts 162 and 164 may focus the ion beams IB1 and IB2 generated in the target parts 152 and 154. In detail, the light focusing parts 162 and 164 may include a first light focusing part 162 focusing the first ion beam IB1 and a second light focusing part 164 focusing the second ion beam IB2. Each of the first light focusing part 162 and the second light focusing part 164 may a magnetic lens. The first light focusing part 162 may select the first ion beam IB1 according to energy. The second light focusing part 164 may select the second ion beam IB2 according to the energy. The first ion beam IB1 selected by the first light focusing part 162 and the second ion beam IB2 selected by the second light focusing part 164 may have different energy.

The patient support unit 300 may be disposed on the beam generation unit 100. However, the embodiment of the inventive concept is not limited thereto. Unlike FIG. 1, the patient support unit 300 may be disposed on one side of the beam generation unit 100. Hereinafter, the structure in which the patient support unit 300 is disposed on the beam generation unit 100 will be described.

The beam transmission unit 200 may receive the ion beams IB1 and IB2 generated from the beam generation unit 100 to irradiate the received ion beams IB1 and IB2 to the target point. The beam transmission unit 200 may include a first path adjusting part 210 that adjusts the path of the first ion beam IB1 to irradiate the first ion beam IB1 to a patient to be treated (hereinafter, referred to as a treated patient TP) and a second path adjusting part 220 that adjusts the path of the second ion beam IB2 to irradiate the second ion beam IB2 to the treated patient TP. The first path adjusting part 210 may extend from one side of the beam generation unit 100 to an upper side of the patient support unit 300. The second path adjusting part 220 may extend from one side of the beam generation unit 100 to an upper side of the patient support unit 300. Each of the first path adjusting part 210 and the second path adjusting part 220 may be a beam guide. The first and second path adjusting parts 210 and 220 may provide paths along which the first ion beam IB1 and the second ion beam IB2 travel, respectively. For example, the first path adjusting part 210 and the second path adjusting part 220 may transmit the first ion beam IB1 and the second ion beam IB2 from the one side of the beam generation unit 100 to the upper side of the patient support unit 300.

The first path adjusting part 210 may include a first injection part 212 provided above the patient support unit 300, and the second path adjusting part 220 may include a second injection part 222 provided above the patient support unit 300. The first injection part 212 may be connected to an end of the first path adjusting part 210 above the patient support unit 300, and the second injection part 222 may be connected to an end of the second path adjusting part 220 above the patient support unit 300. The first and second injection parts 212 and 222 may directly irradiate the first ion beam IB1 and the second ion beam IB2 to the target point. The path of the first ion beam IB1 injected by the first injection part 212 and the path of the second ion beam IB2 injected by the second injection part 222 may do not overlap each other.

Figure 3:
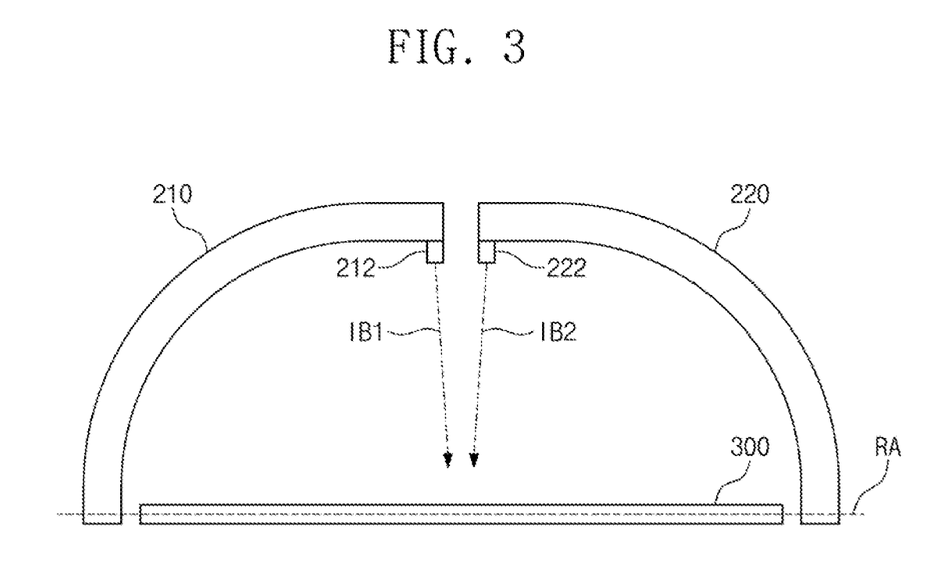
FIGS. 3 to 5 illustrate schematic views for explaining a beam transmission unit.
Figure 4:
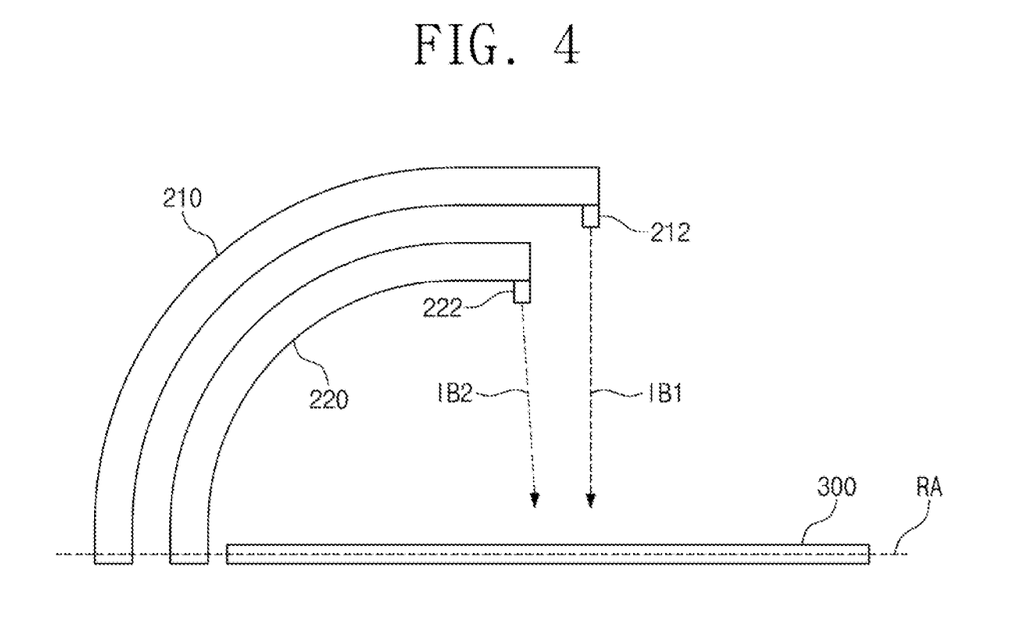
Figure 5:
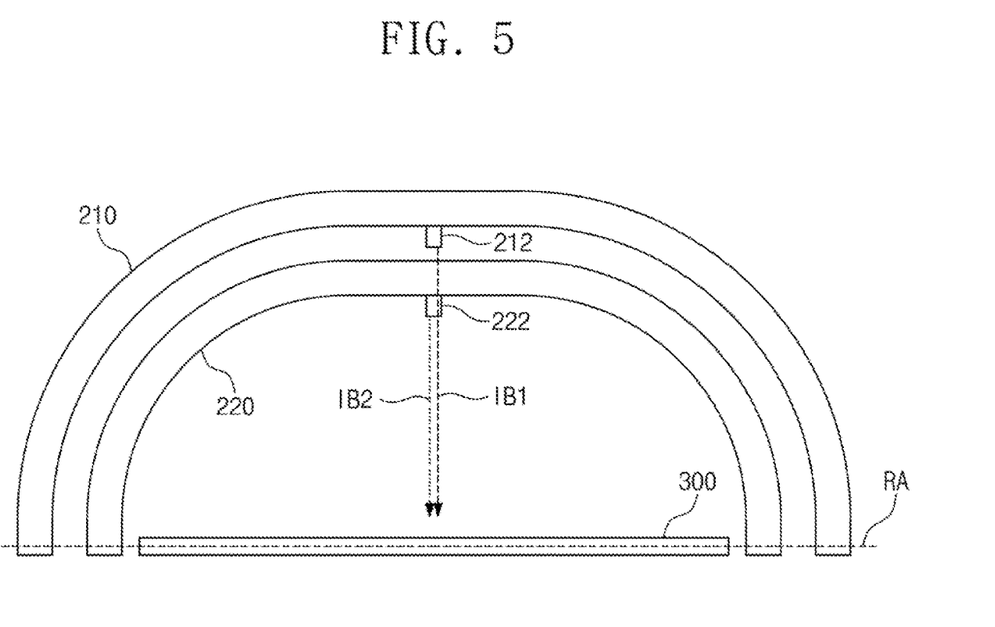
Figure 6:
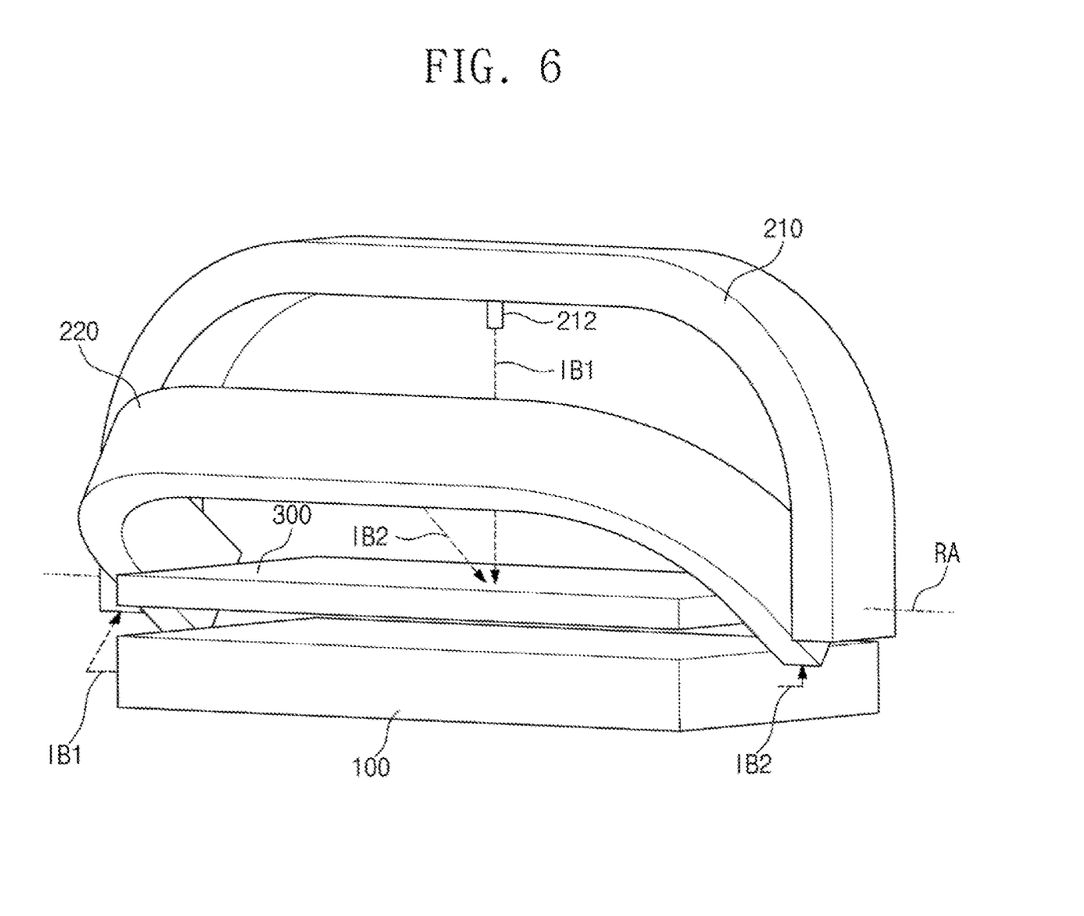
FIG. 6 illustrates a perspective view for explaining the beam transmission unit.

The beam transmission unit 200 may include a gantry. That is, the beam transmission unit 200 may rotate around the patient support unit 300 to irradiate the first and second ion beams IB1 and IB2 to the treated patient PT at various angles. Hereinafter, a configuration of the beam transmission unit will be described in detail with reference to the accompanying drawings. FIGS. 3 to 5 are schematic views for explaining the beam transmission unit. FIG. 6 is a perspective view for explaining the beam transmission unit.

As illustrated in FIG. 3, the first path adjusting part 210 may be disposed on one side of the beam generation unit 100, and the second path adjusting part 220 may be disposed on the other side of the beam generation unit 100. On the other hand, as illustrated in FIG. 4, the first path adjusting part 210 and the second path adjusting part 220 may be disposed on the same side of the beam generation unit 100. Unlike the above-described structure, the first path adjusting part 210 and the second path adjusting part 220 may extend from both sides of the beam generation unit 100 to the upper side of the patient support unit 300.

Referring to FIGS. 5 and 6, the first path adjusting part 210 and the second path adjusting part 220 may rotate. Here, a rotation axis RA of each of the first path adjusting part 210 and the second path adjusting part 220 may be disposed on a plane parallel to a top surface of the patient support unit 300. Although the first path adjusting part 210 and the second path adjusting part 220 have the same rotation axis RA, the embodiment of the inventive concept is not limited thereto. Each of the first path adjusting part 210 and the second path adjusting part 220 may rotate around the rotation axis RA at an angle of about 360 degrees. The rotation path of the first path adjusting part 210 and the rotation path of the second path adjusting part 220 may not overlap each other. The first injection part 212 of the first path adjusting part 210 and the second injection part 222 of the second path adjusting part 220 may rotate around the patient support unit 300. Thus, the first injection part 212 and the second injection part 222 may irradiate the first ion beam IB1 and the second ion beam IB2 to the treated patient TP at various angles.

According to embodiments of the inventive concept, the ion beam treatment apparatus may generate the plurality of ion beams IB1 and IB2 from one pulse laser PL to irradiate the plurality of ion beams IB1 and IB2 to the treated patient TP. In addition, in the ion beam treatment apparatus, the ion beams IB1 and IB2 irradiated to the treated patient TP at the same time may have different energy. Also, the ion beam treatment apparatus may irradiate the plurality of ion beams IB1 and IB2 to the treated patient TP at various angles. Thus, the ion beam treatment apparatus may treat the plurality of targets or perform the treatment under various conditions to improve the treatment efficiency.

In the ion beam treatment apparatus according to the embodiments of the inventive concept, the plurality of ion beams may be generated from the one pulse laser, and the ion beam treatment apparatus may irradiate the plurality of ion beams to the treated patient. In addition, in the ion beam treatment apparatus, the ion beams irradiated onto the treated patient at the same time may have different energy. Also, the ion beam treatment apparatus may irradiate the plurality of ion beams to the treated patient at various angles. Thus, the ion beam treatment apparatus may treat the plurality of targets or perform the treatment under various conditions to improve the treatment efficiency.

Although the embodiment of the inventive concept is described with reference to the accompanying drawings, those with ordinary skill in the technical field of the inventive concept pertains will be understood that the present disclosure can be carried out in other specific forms without changing the technical idea or essential features. Therefore, the above-disclosed embodiments are to be considered illustrative and not restrictive.

What is claimed is:

1. An ion beam treatment apparatus comprising:
a laser generating part;
a dividing part dividing a pulse laser beam generated in the laser generating part into a first laser beam and a second laser beam;
a first target part receiving the first laser beam from the dividing part to generate a first ion beam;
a second target part receiving the second laser beam from the dividing part to generate a second ion beam;
a first path adjusting part adjusting a path of the first ion beam to irradiate the first ion beam to a treated patient; and
a second path adjusting part adjusting a path of the second ion beam to irradiate the second ion beam to the treated patient,
wherein the first path adjusting part and the second path adjusting part rotate with the same rotation axis, and each of the first path adjusting part and the second path adjusting part rotates around the treated patient.

2. The ion beam treatment apparatus of claim 1, further comprising:
a first amplifying part amplifying the first laser beam between the dividing part and the first target part; and
a second amplifying part amplifying the second laser beam between the dividing part and the second target part.

3. The ion beam treatment apparatus of claim 2, wherein a pulse of the first laser beam amplified by the first amplifying part and a pulse of the second laser beam amplified by the second amplifying part are shifted within one period of a pulse of the pulse laser beam.

4. The ion beam treatment apparatus of claim 3, wherein the pulse of the first laser beam amplified by the first amplifying part and the pulse of the second laser beam amplified by the second amplifying part are shifted by about ½ period of the pulse of the pulse laser beam.

5. The ion beam treatment apparatus of claim 1, wherein the first laser beam and the second laser beam travel in directions opposite to each other with respect to the dividing part.

6. The ion beam treatment apparatus of claim 1, wherein the rotation path of the first path adjusting part and the rotation path of the second path adjusting part do not overlap each other.

7. The ion beam treatment apparatus of claim 1, further comprising a light focusing part disposed between the first target part and the first path adjusting part or between the second target part and the second path adjusting part.

8. The ion beam treatment apparatus of claim 1, wherein the dividing part comprises a switching mirror.

9. The ion beam treatment apparatus of claim 1, further comprising a light collecting part disposed between a first amplifying part and the first target part or between a second amplifying part and the second target part.

10. An ion beam treatment apparatus comprising:
a switching mirror receiving a pulse laser from a laser generating part;
a target part receiving a first laser beam and a second laser beam from the switching mirror, wherein the target part receives the first laser beam and the second laser beam to generate a first ion beam and a second ion beam;
a path adjusting part controlling paths of the first ion beam and the second ion beam to irradiate the first and second ion beams to a treated patient; and
a patient support unit on which the treated patient is located,
wherein the laser generating part, the switching mirror, and the target part are provided in a beam generation unit below the patient support unit.

11. The ion beam treatment apparatus of claim 10, wherein the path adjusting part comprises:
a first path adjusting part providing a path along which the first ion beam travels; and
a second path adjusting part providing a path along which the second ion beam travels.

12. The ion beam treatment apparatus of claim 11, wherein the traveling path of the first ion beam does not overlap the traveling path of the second ion beam.

13. The ion beam treatment apparatus of claim 11, wherein the first path adjusting part and the second path adjusting part are opposite to each other with respect to the treated patient.

14. The ion beam treatment apparatus of claim 11, wherein the first path adjusting part and the second path adjusting part rotate around the treated patient.

15. An ion beam treatment apparatus comprising:
   a laser generating part;
   a dividing part dividing a pulse laser beam generated in the laser generating part into a first laser beam and a second laser beam;
   a first target part receiving the first laser beam from the dividing part to generate a first ion beam;
   a second target part receiving the second laser beam from the dividing part to generate a second ion beam;
   a first amplifying part amplifying the first laser beam between the dividing part and the first target part;
   a second amplifying part amplifying the second laser beam between the dividing part and the second target part;
   a first path adjusting part adjusting a path of the first ion beam to irradiate the first ion beam to a treated patient;
   a second path adjusting part adjusting a path of the second ion beam to irradiate the second ion beam to the treated patient.

16. The ion beam treatment apparatus of claim 15, wherein a pulse of the first laser beam amplified by the first amplifying part and a pulse of the second laser beam amplified by the second amplifying part are shifted within one period of a pulse of the pulse laser beam with respect to each other.

17. The ion beam treatment apparatus of claim 16, wherein the pulse of the first laser beam amplified by the first amplifying part and the pulse of the second laser beam amplified by the second amplifying part are shifted by about ½ period of the pulse of the pulse laser beam with respect to each other.

18. The ion beam treatment apparatus of claim 15, wherein the first path adjusting part and the second path adjusting part rotate with the same rotation axis, and each of the first path adjusting part and the second path adjusting part rotates around the treated patient.

* * * * *